United States Patent [19]
Batra et al.

[11] Patent Number: 6,046,182
[45] Date of Patent: Apr. 4, 2000

[54] STEROID CARBAMATES AS POTENTIATING AGENTS

[75] Inventors: Satish Batra, Lund; Jan-Inge Carlsson, Helsingborg; Thomas Fex, Lund, all of Sweden

[73] Assignee: Satish BATRA, Lund, Sweden

[21] Appl. No.: 09/120,306

[22] Filed: Jul. 22, 1998

[30] Foreign Application Priority Data

Jan. 23, 1996 [SE] Sweden ................................. 9600229

[51] Int. Cl.$^7$ .............................. A61K 31/56; C07J 5/00; C07J 7/00
[52] U.S. Cl. ........................ 514/169; 514/177; 514/182; 552/557; 552/582; 552/586; 552/590
[58] Field of Search ................... 552/557, 590, 552/582, 586; 514/177, 169, 182

[56] References Cited

U.S. PATENT DOCUMENTS

| | | | |
|---|---|---|---|
| 3,787,453 | 1/1974 | Fahrenholtz | 260/397.4 |
| 4,772,594 | 9/1988 | Hashimoto et al. | 514/178 |

FOREIGN PATENT DOCUMENTS 9322677  11/1993  WIPO.

OTHER PUBLICATIONS

Van dort et al. (CA 112:51377, abstract of Nucl. Med. Biol. (1989), vol. 16(6), 603–7).
Petrow et al. (CA106:693, abstract of Prostate (N.Y.) (1986), 9(2), 169–82).
Petrow, V. et al., "Design of Cytotoxic Steroids for Prostate Cancer," *The Prostate* 9:169–182 (1986).
Van Dort, M. et al., "Potential Tumor or Organ Imaging Agents—31. Radioiodinated Sterol Benzoates and Carbamates," *Nucl. Med. Biol.* 16–6:603–607 (1989).
Werbin, H. et al., "Steroid Alpha–Naphthylurethans," *Journal of the American Chemical Society* 77:4431–4432 (1955).
Wintersteiner O., et al., "Crystalline Progestin," *The Journal Of Biological Chemistry* 107–1:321–336 (1934).

Primary Examiner—Jose' G. Dees
Assistant Examiner—Sabiha Qazi
Attorney, Agent, or Firm—Browdy and Neimark

[57] ABSTRACT

Novel potentiating steroid carbamates having the general formula (I)

$$ST\text{-}OCONR_1R_2 \qquad (I)$$

wherein ST is a steroid or steroid derivative, of the structure (II)

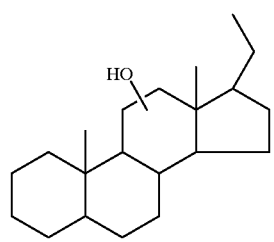

(II)

optionally containing double bonds and additional oxygen substituents; the carbamate moiety $OCONR_1R_2$ has lipophilic properties and is selected from N,N-dibutylcarbamate, N-(3-morpholin-4-yl-propyl)-carbamate, 4-benzyl-piperazine-1-carboxylic acid ester, N-(3-dibutylamino-propyl)-carbamate, N,N-dipropyl-carbamate, N-hexyl-carbamate, N-(1-benzyl-piperidine-4-yl)-carbamate, N-cyclohexylmethyl-carbamate, N-butyl-N-ethyl-carbamate, N-benzyl-carbamate, N-(3-dibenzazepin-1-yl-propyl)-N-methyl-carbamate, N-naphtalen-1-yl-methyl-carbamate, N-diphenylmethyl-carbamate, N,N-dibenzyl-carbamate, 3,4-dihydro-1H-isoquinoline-2-carboxylic acid ester, N,N-dipentyl-carbamate, N,N-diisobutyl-carbamate and N,N-bis-(4-fluoro-benzyl)-carbamate; and pharmaceutically acceptable salts thereof, in combination with radiation therapy and one or more cytotoxic drugs, optionally together with a pharmaceutically acceptable carrier and, if desired, other pharmacologically acceptable agents.

8 Claims, 1 Drawing Sheet

OTHER PUBLICATIONS

Abstract of Yu, C.–N. et al., "Novel urethane–containing aminosteroid compounds," (1995).

Overman, L.E. et al., "Mild Procedures for Interconverting Allylic Oxygen Functionally. Cyclization–Induced [3,3] Sigmatropic Rearrangement of Allylic Carbamates," *Journal Of American Chemical Society* 100–15:4822–4834 (1978).

STEROID CARBAMATES AS POTENTIATING AGENTS

The present invention relates to novel steroid derivatives which potentiate the activity of various cytotoxic drugs and of radiation therapy.

BACKGROUND

Chemotherapy failure remains a significant problem in the treatment of neoplastic disease. Despite initial sensitivity to chemotherapy most tumors become unresponsive during prolonged treatment. This is thought to be due to the outgrowth of drug resistant mutant tumor cells, and is referred to as acquired resistance. Conversely, some tumors appear to be insensitive to therapy from the onset and these are intrinsically resistant.

Both acquired or intrinsic resistance are characterised by the development of resistance to different groups of drugs with no apparent structural or functional similarities, such as vinca alkaloids and anthracyclines. Although the cellular mechanism of drug resistance is multi-factorial, the ability of resistant cells to lower the intracellular concentration of drug appears to be the most common mechanism.

Several agents of diverse chemical structures are known to potentiate the uptake and the cellular toxicity of cytotoxic drugs such as vinca alkaloids and anthracyclines. This is of great clinical importance in the treatment of cancer, particularly as tumors which have developed resistance to chemotherapy may again become sensitive when treated with a cytotoxic drug in combination with a potentiating agent.

PRIOR ART

Verapamil was one of the first compounds for which the potentiating properties were observed (A. M. Rogan et al., Science 224, p. 994–996, 1984). The structure and synthesis of verapamil are disclosed in U.S. Pat. No. 3,261,859 (DENGEL FERDINAND). The potentiating effect which was quite marked in experimental systems could however not be reproduced in the clinic, primarily due to dose-limiting side effects occuring at the high doses of verapamil that are required for potentiation.

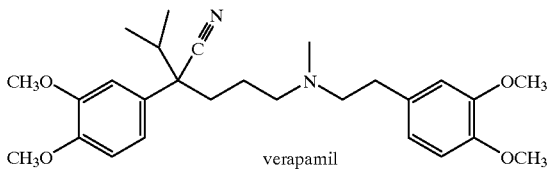

verapamil

For several other registered drugs where potentiating properties have been observed, the side effects have also been dose-limiting and have prevented their clinical use as potentiating agents.

RO 11-2933 is a tiapamil analog which has shown in vivo activity when tested in combination with doxorubicin (J. A. Plumb et al., Biochemical Pharmacology, 2, p. 257–266, 1994). The structure and synthesis of RO 11-2933 are disclosed in GB 1489088 (HOFFMANN-LA ROCHE AG).

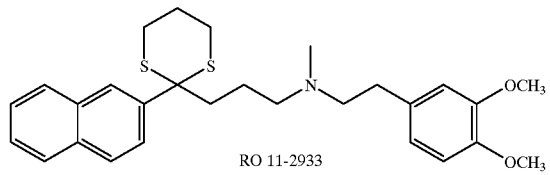

RO 11-2933

Estramustine, widely used in the treatment of prostate cancer, and which is a cytotoxic steroid derivative where estradiol is coupled to nor-nitrogen mustard via a carbamate bridge, was recently shown to possess weak potentiating activity (S. C. Batra et al, Urological Research 23 p. 286, 1995). The structure and synthesis of estramustine are disclosed in U.S. Pat. No. 3,299,104 (FEX ET AL).

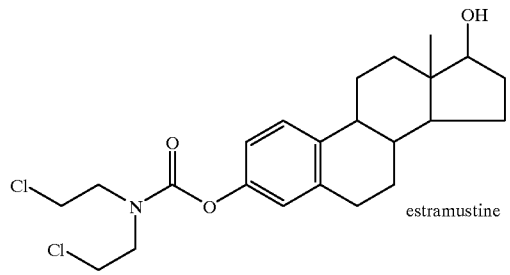

estramustine

Estramustine has also been shown to potentiate radiation effects on tumors in animal models (S. Eklöv et al., The Prostate, 24, p. 39–45, 1994).

WO 95/08559 (PROCTER & GAMBLE) describes urethane containing aminosteroid compounds for the treatment of congestive heart failure. The carbamate residue is located in the 3-position. None of the compounds described is noted for potentiating activity.

L. E. Overman et al., J.Am.Chem.Soc. (1978) 100 (15), 4822–34, describe a N,N-dimethyl carbamate steroid derivative used in a chemical study of a cyclization induced [3,3] sigmaotropic rearrangement of allylic carbamates.

U.S. Pat. No. 4,772,594 (FUJISAWA) describes prodrugs wherein a biologically active substance (e.g. antitumor compound) is coupled to a steroid via a carbamate linker. The steroid is utilized only as a carrier.

Patent application WO92/18089 (ABRAHAM ET AL) describes steroidal amines which have the ability to sensitize multidrug resistant cancer cells. However no steroid carbamates are included.

There is obviously a great need for new nontoxic compounds having strong potentiating properties

OBJECTS OF THE INVENTION

We have found steroid carbamates having superior potentiating properties without being cytotoxic.

Accordingly, one object of the present invention is to provide new potentiating compounds having the general formula (I).

A second object is to provide compounds of general formula (I) wherein the steroid moiety itself possesses none or little adverse biologic activity.

A third object is to provide processes for preparing the new compounds according to the first, and second objects.

A fourth object is to provide compositions containing as an active ingredient one or more of the compounds of general formula (I), preferably together with a pharmaceutically acceptable carrier and, if desired, other pharmaceutically active ingredients.

A fifth object of the invention is to provide methods of treating diseases by administering one or more compounds having the general formula (I) in combination with other biologically active compounds.

Other objects of the invention will become apparent to one skilled in the art, and still further objects will become apparent hereinafter.

SUMMARY OF THE INVENTION

The present invention relates to novel steroid carbamates having the general formula (I)

ST-OCONR$_1$R$_2$ (I)

wherein ST is a steroid or steroid derivative of the structure (II)

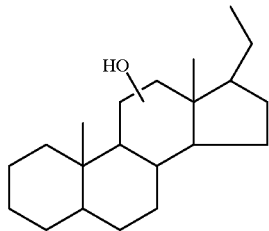

(II)

optionally containing double bonds and additional oxygen substituents; the carbamate moiety OCONR$_1$R$_2$ has lipophilic properties and is selected from N,N-dibutylcarbamate, N-(3-morpholin-4-yl-propyl)-carbamate, 4-benzyl-piperazine-1-carboxylic acid ester, N-(3-dibutylamino-propyl)-carbamate, N,N-dipropyl-carbamate, N-hexyl-carbamate, N-(1-benzyl-piperidine-4-yl)-carbamate, N-cyclohexylmethyl-carbamate, N-butyl-N-ethyl-carbamate, N-benzyl-carbamate, N-(3-dibenzazepin-1-yl-propyl)-N-methyl-carbamate, N-naphtalen-1-yl-methyl-carbamate, N-diphenylmethyl-carbamate, N,N-dibenzyl-carbamate, 3,4-dihydro-1H-isoquinoline-2-carboxylic acid ester, N,N-dipentyl-carbamate, N,N-diisobutyl-carbamate, and N,N-bis-(4-fluoro-benzyl)-carbamate.

Compounds wherein R$_1$ and/or R$_2$ contain an ionizable group can be in the form of addition salts with appropriate pharmaceutically acceptable inorganic or organic counterions.

As regards ST those compounds are preferred wherein ST is a steroid or steroid derivative which by itself possesses no or little biologic activity.

Preferably ST by itself has no or little estrogenic, androgenic, glucocorticoid or mineralocorticoid effects.

Compounds wherein ST is a steroid derivative of the structure (II) below, optionally containing double bonds and additional oxygen substituents, are preferred, especially progesterone and pregnenolone derivatives.

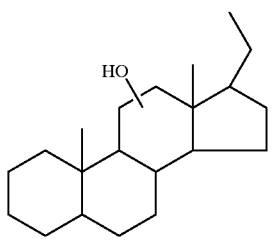

(II)

the carbamate moiety OCONR$_1$R$_2$ is as defined above and has lipophilic properties.

Those compounds wherein R$_1$ and/or R$_2$ contain a basic nitrogen have increased water solubility.

METHODS OF PREPARATION

The compounds having the general formula (I) may be prepared by conventional methods.

Method 1.

A steroid derivative of formula (A1) wherein X is a leaving group is reacted with an appropriate amine of formula (B1) to yield the desired structure of formula (I).

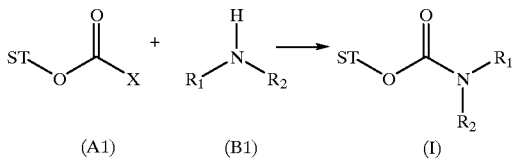

Method 2.

A steroid derivative of formula (A2) is reacted with an isocyanate of formula (B2) to yield a compound of formula (I) wherein R$_2$ is hydrogen. The isocyanate may optionally be generated in situ during the reaction.

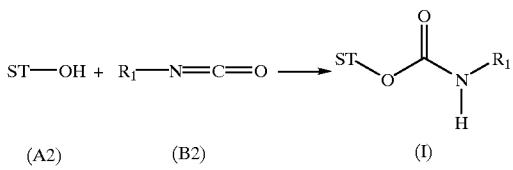

Method 3.

A steroid derivative of formula (A2) is reacted with a carbamate of formula (B3), wherein X is a leaving group, to yield a compound of formula (I)

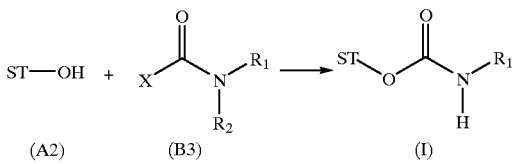

The above mentioned Method 1 is the preferred method of preparation.

Compounds of formula (I) may, if desired, be further modified using reactions and methods well known to the skilled organic chemist.

If desirable, prodrugs may be prepared of the compounds of formula (I), and these are also within the scope of the present invention.

DETAILED DESCRIPTION OF THE INVENTION

Figure 1:
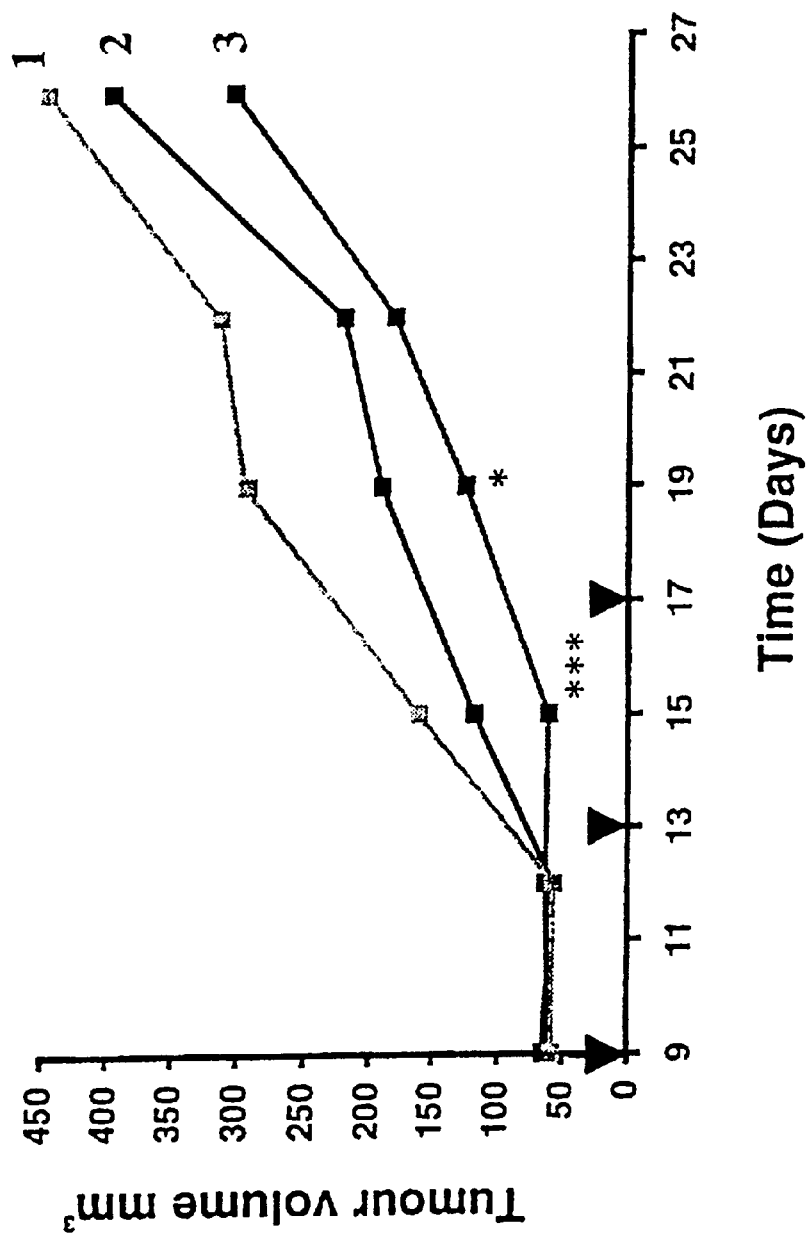

The following examples are intended to illustrate but not to limit the scope of the invention.

These compounds have been designated by numbers in the examples where their systematic names are given. These compounds are later referred to by a number code $a:b_1$ where a means the number of the example wherein the preparation of the compound in question is described, and b refers to the order of the compounds prepared according to that example. Thus, compound 1:2 means the second compound prepared according to Example 1.

The structure of the compounds found in the examples are confirmed by NMR. Melting points were determined on a Koffler melting point apparatus and are uncorrected.

EXAMPLE 1

This example illustrates the preparation of compounds of general formula (I) above by reacting a chloroformate with an amine.

8 g of pregn-4-ene-3,20-dione-11-ol, chlorocarbonyloxy-, was dissolved in 300 ml of $CH_2Cl_2$ and 5.5 g of dibutylamine in 200 ml of $CH_2Cl_2$ was added. The mixture was stirred over night, washed with 2 N HCl and water, dried and the solvents evaporated to yield an oil. Upon addition of ether 6.0 g of crystalline pregn-4-ene-3,20-dione-11-yl, N,N-dibutylcarbamate (1:1), mp. 157° C., was obtained.

In essentially the same manner the following compounds are obtained from the corresponding appropriate starting materials:

pregn-5-ene-20-one-3-yl, N-(3-morpholin-4-yl-propyl)-carbamate (1:2), mp. 45–50° C.;
pregn-5-ene-20-one-3-yl, 4-benzyl-piperazine-1-carboxylic acid ester (1:3), mp. 154° C.;
pregn-5-ene -20-one-3-yl, N-(3-dibutylamino-propyl)-carbamate (1:4), amorphous;
pregn-5-ene-20-one-3-yl, N,N-dipropyl-carbamate (1:6), mp. 131° C.;
pregn-5-ene-20-one-3-yl, N-hexyl-carbamate (1:7), amorphous;
pregn-5-ene-20-one-3-yl, N-(1-benzyl-piperidine-4-yl)-carbamate (1:8), mp. 145° C.;
pregn-4-ene-3-one-20-yl, N-(3-morpholin-4-yl-propyl)-carbamate (1:9) mp. 112° C.;
pregn-4-ene-3-one-20-yl, N-hexyl-carbamate (1:11), amorphous;
pregn-4-ene-3-one-20-yl, N-(1-benzyl-piperidin-4-yl)-carbamate (1:12), amorphous;
pregn-4-ene-3-one-20-yl, N-(3-dibutylamino-propyl)-carbamate (1:13), amorphous;
pregn-4-ene-3-one-20-yl, N,N-dipropyl-carbamate (1:14), amorphous;
pregn-4-ene-3,20-dione-11-yl, N-(3-morpholin-4-yl-propyl)-carbamate (1:15), amorphous;
pregn-4-ene-3,20-dione-11-yl, N-(3-dibutylamino-propyl)-carbamate (1:17), amorphous;
pregn-4-ene-3,20-dione-11-yl, N-hexyl-carbamate (1:18), amorphous;
pregn-4-ene-3,20-dione-11-yl, N,N-dipropyl-carbamate (1:19), mp. 148° C.;
pregn-4-ene-3,20-dione-11-yl, N-(1-benzyl-piperidin-4-yl)-carbamate(1:20), mp. ca 130° C.;
pregn-4-ene-3,20-dione-11-yl, N-cyclohexylmethyl-carbamate (1:23), amorphous;
pregn-4-ene-3,20-dione-11-yl, N-butyl-N-ethyl-carbamate (1:24), amorphous;
pregn-4-ene-3,20-dione-11-yl, N-benzyl-carbamate (1:25), mp. ca 215° C.;
pregn-4-ene-3,20-dione-11-yl, N-(3-dibenzazepin-1-yl-propyl)-N-methyl-carbamate (1:30), mp. 240° C.;
pregn-4-ene-3,20-dione-11-yl, N-naphtalen-1-yl-methyl-carbamate (1:31), mp. ca 240° C.;
pregn-4-ene-3,20-dione-11-yl, 4-benzyl-piperazine-1-carboxylic acid ester (1:33) mp. 200° C.;
pregn-4-ene-3,20-dione-11-yl, N-diphenymethyl-carbamate (1:34), mp. 148° C.;
pregn-4-ene-3,20-dione-11-yl, N,N-dibenzyl-carbamate (1:35), mp. 150° C.;
pregn-4-ene-3,20-dione-11-yl, 3,4-dihydro-1H-isoquinoline-2-carboxylic acid ester (1:36), mp. 155° C.;
pregn-4-ene-3,20-dione-11-yl, N,N-dipentyl-carbamate (1:37), amorphous;
pregn-4-ene-3,20-dione-11-yl, N,N-diisobutyl-carbamate (1:39), mp. 144° C.;
pregn-4-ene-3,20-dione-11-yl, N,N-bis-(4-Fluoro-benzyl)-carbamate (1:40), mp. 176° C.

EXAMPLE 2

This example illustrates the preparation of compounds of general formula (Al) by reacting an appropriate steroid with phosgene.

33 g of pregn-4-ene-3,20-dione-11-ol and 13.2 g of quinoline were dissolved in 300 ml of THF and added to a solution of about 13 g of phosgene in 300 ml of THF. The mixture was stirred at room temperature over night and the solvents were evaporated. The residue was taken up in $CH_2Cl_2$, washed with 2N HCl, dried and the solvents were evaporated to obtain an almost quantitative yield of pregn-4-ene-3,20-dione-11-yl, chloroformate (2:1).

In essentially the same manner the following compounds are obtained from the corresponding appropriate starting materials:

pregn-5-ene-20-one-3-yl, chloroformate (2:2);
pregn-4-ene-3-one-20-yl, chloroformate (2:3).

EXAMPLE 3

This example demonstrates the potentiating effect of compounds of formula (I) in accordance with data in the below Table 1.

Human colon tumor cells (HCT-15) or rat prostatic tumor cells (AT-1) were cultured in RPMI medium containing v/v FCS (10%) penicillin/streptomycin (1.1%), L-glutamine (0.9%), and in the case of AT-1 cells, dexamethasone (250 nM). Both cell lines have an intrinsic resistance to cytotoxic drugs including daunorubicin. Approximately $1 \times 10^4$ cells in log phase were seeded in 12 well plates for 24 hrs in the above medium. The medium was then replaced by a medium containing fixed concentrations of daunorubicin (50 nM and 30 nM for HCT-15 and AT-1 cells respectively) and different concentrations (0.0125–4 microM) of the compounds to be tested and the cells were incubated for 24 hrs. The medium was thereafter changed to a drug free medium and incubated for another 96 hrs. The cells were loosened with 0.25% trypsin, suspended in 1 ml of medium and counted in a Coulter counter. $IC_{50}$ values (concentration required to reduce cell survival by 50%) were calculated.

TABLE 1

| Compound | IC$_{50}$, HCT-15(M) | IC$_{50}$, AT-1(M) |
|---|---|---|
| 1:1 | 0.51 | 0.76 |
| 1:4 | 0.15 | 0.19 |
| 1:13 | 0.28 | 0.21 |
| 1:35 | 0.11 | 0.15 |
| verapamil | 0.5 | 0.74 |
| estramustine | >2.5 | |

EXAMPLE 4

This example demonstrates the potentiating effect of compound 1:1 in vivo as shown by the data in FIG. 1.

Seven- to eight-week-old Severe Combined Immunodeficient (SCID) mice were inoculated s.c. with 3×10$^6$ HCT-15 cells into the left flank. Nine days after tumor cell inoculation animals with palpable tumors were randomized into groups of 10 mice/group. On days 9, 13 and 17 groups of mice were treated with doxorubicin (2 g/kg;i.v.) alone or in combination with compound 1:1 (400 mg/kg; p.o.). Compound 1:1 was given 2 hours before doxorubicin. One group received only vehicle and served as control.

Tumor growth was monitored by measuring tumor size with a calibrated microcapillar twice a week. Tumor volume (V) was calculated by using the formula V=(L×W$^2$/2) where L and W are the long and short diameters (mm) respectively. At day 26 the animals were sacrificed and the tumor weight measured.

FIGURE LEGEND

FIG. 1 relates to Example 4 and shows growth of human colon cell line HCT-15 on a subcutaneous xenograft in SCID mice. Mice were treated with vehicle (1) or doxorubicin (2) or doxorubicin plus compound 1:1 (3) at day 9, 13 and 17 following inoculation of the HCT-15 cells (arrows). Significance of difference between (1) and (2) is indicated by * being p<0.05 and *** being p<0.005.

The compounds of formula (I) potentiate the activity of cytotoxic drugs both in vitro and in vivo and can with advantage be used in combination with these for cancer treatment.

Potentiating agents may be used as reversing agents in multidrug resistant tumors and may also be used to prevent or delay the development of resistance.

These agents may also potentiate the effect of radiation therapy.

Potentiating agents are effective in increasing the intracellular concentrations of several types of drugs and could therefore be of interest in many therapeutic areas.

Effective quantities of compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, emulsions, tablets, capsules and powders prepared for oral administration, and sterile solutions for parenteral administration.

A suitable dose may vary between 0.1 mg/kg to about 100 mg/kg body weight, in particular from about 1 mg/kg to about 100 mg/kg once or twice daily depending upon the specific condition to be treated, the age and the weight of the specific patient, and the specific patients response to the medication. The exact individual dosage, as well as the daily dosage, will be determined under the direction of an experienced physician.

Various additives to enhance stability or ease of administration of the drug are contemplated. The pharmaceutical composition may also contain additional therapeutically useful substances others than a compound of formula (I).

What is claimed is:

1. A compound selected from the group consisting of pregn-4-ene-3,20-dione-11-yl, N,N-dibutylcarbamate (1:1), pregn-5-ene-20-one-3-yl,N-(3-dibutylamino-propyl)-carbamate (1:4), pregn-4-ene-3-one-20-yl,N-(3-dibutylamino-propyl)-carbamate (1:13), pregn-4-ene-3,20-dione-11-yl,N-(3-dibutylamino-propyl)-carbamate (1:17), pregn-4-ene-3,20-dione-11-yl,N-naphtalen-1-yl-methyl-carbamate (1:31), pregn-4-ene-3,20-dione-11-yl,N-diphenylmethyl-carbamate (1:34), pregn-4-ene-3,20-dione-11-yl,N,N-dibenzyl-carbamate (1:35), pregn-4-ene-3,20-dione-11-yl,N,N-diisobutyl-carbamate (1:39), and pregn-4-ene-3,20-dione-11-yl,N,N-bis-(4-fluoro-benzyl)-carbamate (1:40).

2. Pharmaceutical composition comprising one or more compounds according to claim 1.

3. Pharmaceutical composition according to claim 2 which potentiates the activity of cytotoxic drugs.

4. Pharmaceutical composition according to claim 2 for use as reversing agent in multidrug resistant tumors and/or for preventing or delaying the development of resistance in such tumors.

5. Pharmaceutical composition according to claim 2 which potentiates the effect of radiation therapy.

6. Pharmaceutical composition according to claim 2 formulated as a solution, an emulsion, a tablet, a capsule or a powder prepared for oral administration, or a sterile solution for parenteral administration.

7. Pharmaceutical composition according to claim 2 for administration in a dosage of from about 0.1 mg/kg to about 100 mg/kg body weight.

8. Pharmaceutical composition according to claim 2 in a dosage amount from about 1 mg/kg to about 100 mg/kg body weight once or twice daily.

* * * * *

UNITED STATES PATENT AND TRADEMARK OFFICE
CERTIFICATE OF CORRECTION

PATENT NO.  : 6,046,182
DATED       : April 4, 2000
INVENTOR(S) : Batra et al.

It is certified that error appears in the above-identified patent and that said Letters Patent is hereby corrected as shown below:

Title page,
Line [22], below "Filed" insert --PCT Filed: Jan. 17, 1997--;
After line [22] insert --[86] Continuation of PCT/SE97/00066--;
[87] PCT Pub. No.: WO97/27211
     PCT Pub. Date: Jul. 31, 1997--.

Signed and Sealed this

Third Day of July, 2001

*Attest:*

NICHOLAS P. GODICI
*Attesting Officer*    *Acting Director of the United States Patent and Trademark Office*